(12) United States Patent
Cullum et al.

(10) Patent No.: US 7,408,640 B2
(45) Date of Patent: Aug. 5, 2008

(54) FLUORESCENCE POLARIZATION INSTRUMENTS AND METHODS FOR DETECTION OF EXPOSURE TO BIOLOGICAL MATERIALS BY FLUORESCENCE POLARIZATION IMMUNOASSAY OF SALIVA, ORAL OR BODILY FLUIDS

(75) Inventors: Malford E. Cullum, Grayslake, IL (US); Lloyd G. Simonson, Spring Grove, IL (US); Sylvia Z. Schade, Riverside, IL (US); Linda A. Lininger, Grayslake, IL (US); Alan L. McArthur, Mokena, IL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 449 days.

(21) Appl. No.: 10/700,868

(22) Filed: Nov. 5, 2003

(65) Prior Publication Data

US 2005/0095601 A1    May 5, 2005

(51) Int. Cl.
*G01J 3/00* (2006.01)
*G01J 4/00* (2006.01)
*C12M 1/00* (2006.01)
*C12M 3/00* (2006.01)

(52) U.S. Cl. .................. 356/368; 356/300; 356/364; 435/283.1; 435/287.1; 435/287.2

(58) Field of Classification Search ............. 424/184.1, 424/1.11, 10.1; 436/500, 543, 546
See application file for complete search history.

(56) References Cited

U.S. PATENT DOCUMENTS 4,516,856 A * 5/1985 Popelka .................. 356/368
6,052,187 A * 4/2000 Krishnan et al. ........... 356/364

* cited by examiner

*Primary Examiner*—N. M. Minnifield
*Assistant Examiner*—Vanessa L Ford
(74) *Attorney, Agent, or Firm*—Ning Yang; Joseph K. Hemby (57) ABSTRACT

The inventive subject matter relates to a method for detecting the presence of a biological substance of interest in a test sample of saliva or oral fluid, comprising combining said test sample with a fluorescence-labeled ligand to said biological substance and detecting a change in the fluorescence polarization of said test sample produced by binding of said fluorescence-labeled ligand to said biological substance. In one aspect of the inventive subject matter, said method comprises additional steps for comparing the fluorescence polarization of said test sample with the fluorescence polarization of a control solution. Also provided is a miniaturized, portable apparatus for measuring the fluorescence polarization of a liquid sample.

1 Claim, 3 Drawing Sheets

FLUORESCENCE POLARIZATION INSTRUMENTS AND METHODS FOR DETECTION OF EXPOSURE TO BIOLOGICAL MATERIALS BY FLUORESCENCE POLARIZATION IMMUNOASSAY OF SALIVA, ORAL OR BODILY FLUIDS

BACKGROUND OF THE INVENTION

1. Field of Invention

The present inventive subject matter relates to novel methods for detecting the presence of a biological substance of interest in a test sample of saliva, oral or other bodily fluids. Also provided is a miniaturized, portable, hand-held apparatus for measuring the fluorescence polarization of a liquid sample.

2. Description of the Related Art

Immunoassays. Infectious disease rates and immunization strategies continue to evolve in the United States and worldwide in response to societal needs, national defense, and evolutionary changes in the organisms producing disease. Immunizations are performed to prevent many infections, while prophylactic population screening is utilized for infections lacking effective vaccines and for those diseases having a low enough incidence that mass immunization is not deemed most efficacious.

The current method for diagnosis of disease, determining exposure to biological materials such as pathogens, or monitoring immunization status varies depending on the specific assay. Some methods employ an in vivo assay. Others require a biological sample, such as blood or serum, to be obtained and tested. Tests performed usually are one of the non-homogeneous type diagnostic methods such as enzyme-linked immunosorbant assay (hereinafter "ELISA"), radioimmunoassay (hereinafter "RIA"), or agglutination. All are surface-binding, heterogeneous assays and require the antigen of interest to interact with a surface to achieve success, often at the expense of high non-specific binding and loss of specificity.

Fluorescence Polarization

Fluorescence polarization (hereinafter "FP") is the process in which visible or ultraviolet light is polarized with a filter and shines on part of a molecule, the fluorochrome, that in turn fluoresces, emitting light of longer wavelength whose signal is captured and recorded. The emitted light recorded stays more polarized in solutions when there are slower turning, large molecule-fluorochrome complexes than when there are smaller labeled molecules. Different fluorochromes can be chosen to accommodate molecules of different sizes up to $10^7$ kDa molecular weight.

U.S. Pat. No. 4,585,862 to Wang, et al., issued Apr. 29, 1986, discloses a method and reagents for determining a ligand, particularly steroid, hormone, antiasthmatic, antineoplastic, antiarrhythmic, anticonvulsant, antibiotic, antiarthritic, antidepressant, cardiac glycoside, or a metabolite thereof, in biological fluids such as serum, plasma, spinal fluid, amnionic fluid, and urine. In particular, Wang, et al. relates to a specific class of tracer compounds required as reagents in such procedures.

U.S. Pat. No. 5,976,820 to Jolley, et al., issued Nov. 2, 1999, discloses a homogeneous immunoassay in which a fluorophore-conjugated lipopolysaccharide derived bacterial antigen is reacted with antibodies specific for the antigens in a diluted serum specimen, with quantitative detection of the formation of an immune complex obtained by measuring the change in fluorescence polarization after complex formation.

U.S. Pat. No. 6,432,632 to Nakayama, et al., issued Aug. 13, 2002, discloses a fluorescence polarization method for analyzing an assay-object in a sample, comprising the steps of: (a) providing a fluorescent-labeled protein in which a protein is covalently bound to a fluorochrome(s), wherein the protein is capable of specifically binding to the assay-object; (b) allowing the fluorescent-labeled protein to bind to the assay-object; and (c) measuring a change in the degree of fluorescence polarization which has taken place in the fluorescent-labeled protein by its binding to the assay-object.

Saliva and Oral Fluids

Saliva and oral fluids are biochemically distinct and have been increasingly recognized as acceptable alternatives to serum for use in diagnostic tests for certain hormones, drugs, antibodies and antigens. Oral fluids are collected without pain, needle sticks, or religious and social prohibitions, and their use involves minimal risk or exempt protocols for the use of human subjects. Surprisingly, diagnostic assays utilizing saliva and other oral fluids appear as entries in the National Library of Medicine MEDLARS database with a frequency of only 1 in 30 and 1 in 100, respectively, when compared to entries in which blood serum is reported.

Knowledge of the epidemiology of diseases is important in health care planning and treatment. Both are dependent upon accurate and rapid diagnosis. Using an under-utilized and elegant technology, fluorescence polarization, we have developed assays for accurate and rapid detection and diagnosis of antibodies to pathogens producing diseases of military and commercial interest. The technology is homogeneous and can accurately estimate concentrations of diagnostic markers, drugs and chemicals, or bio-hazardous agents in oral fluids and environmental samples within a few seconds to several minutes. Further, the inventive oral immunodiagnostic assay systems are robust and relatively unaffected by use with non-homogeneous samples, such as whole blood or saliva. Specificity of FP assays is generally very high, approximately 98%, with good sensitivity. The applications of FP salivary diagnostics to determination of tuberculosis exposure and of anthrax immunization status are provided as examples.

There is potential for widespread use of these assays as non-invasive tests, especially as more compact, simplified fluorescence polarimeters become available. FP tests are provided and are applicable to a wide spectrum of microorganisms. Rapid FP salivary diagnostics, have both military and civilian applications and may be used in a clinic or field setting to aid in diagnosis of disease, detection of exposure, or verification of vaccination. Particularly in those instances where rapid detection in field situations is required, these considerations and continuing improvements in standardization of collection methods make the use of saliva and oral fluids as well as bodily fluids a novel and effective diagnostic media of choice for the future.

Fluorescence Polarization Detection Instrumentation

Fluorescence polarization instruments and their use for clinical applications are described, for example, in "Design, Construction, and Two Applications for an Automated Flow-Cell Polarization Fluorometer with Digital Read Out"; R. D. Spencer, F. D. Toledo, B. T. Williams, and N. L. Yoss; Clinical Chemistry, 19/8, pages 838-344 (1973). Such instruments can rapidly analyze body fluid samples labeled with a fluorescent material.

Early instruments of such type required relatively high wattage, intense light sources, such as 200-250 watt mercury or xenon gas discharge lamps, in order to obtain the desired emission radiation from the sample at a signal to noise level ratio sufficient for detection and amplification by a low-noise photomultiplier tube and associated electronics. Such high wattage, bright lamps also require substantial cooling in order to maintain the integrity of the optical system.

Figure 1:
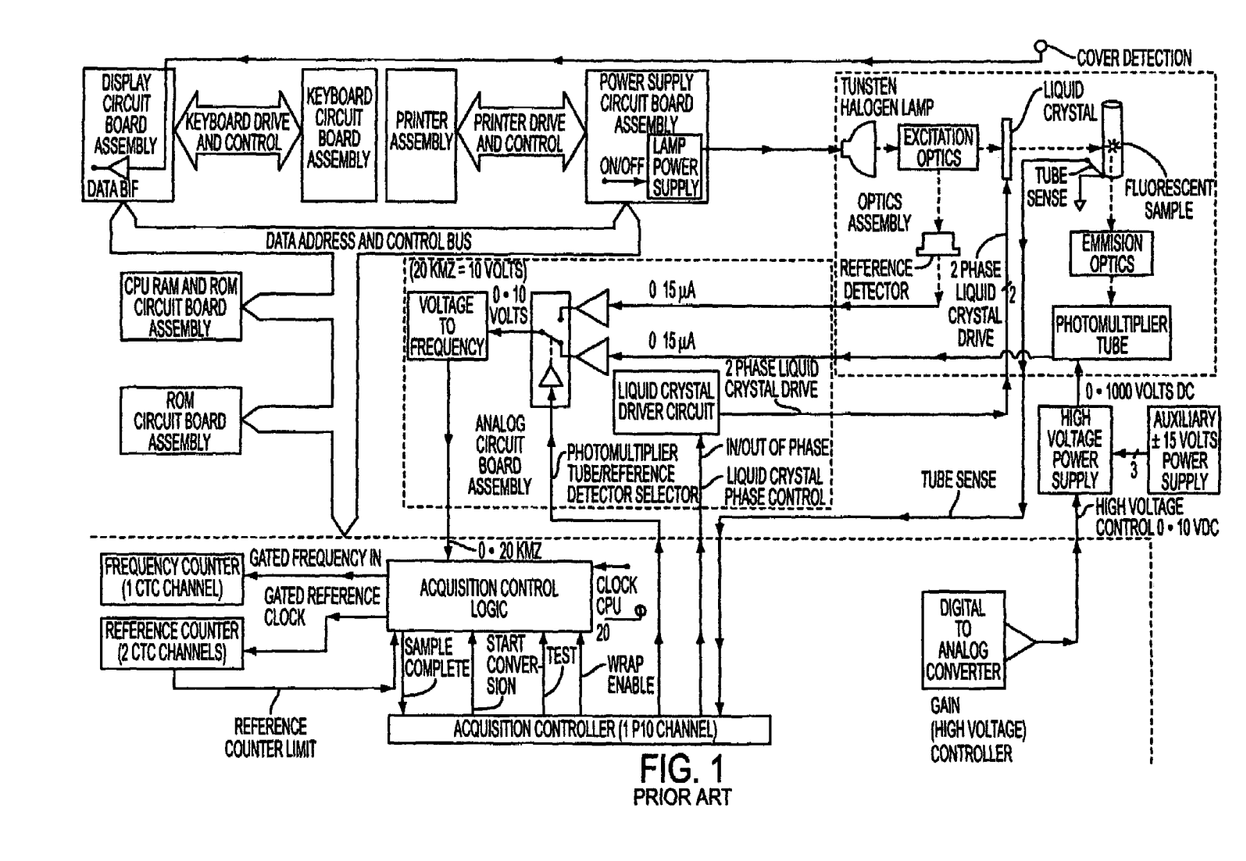
FIG. 1 is a drawing which depicts the layout and components of a prior art fluorescence polarization instrument.

An improved fluorescence polarization instrument is described in U.S. Pat. No. 4,516,856, issued to Popelka on May 14, 1985. Popelka discloses an optical system for a fluorescent polarization instrument including a low wattage, low intensity focused light source and a polarizer/liquid crystal combination in the excitation path focusing excitation light of alternate planes of perpendicular polarization onto a fluorescent liquid sample, wherein emitted light from the fluorescent sample is filtered, polarized and focused onto a photomultiplier for processing, and a series of non-reflective baffles are placed around the sample to reduce reflections; monitoring means monitor the excitation light and maintain a substantially constant intensity level focused on the sample, while the low wattage, low intensity light source is provided by a 50 watt tungsten halogen projector lamp. An exemplary prior art instrument schematic is shown in FIG. 1.

Even with these improvements, current instruments are large, bulky tabletop instruments with high voltage and high power usage, and thus substantial AC power requirements. Further, current FP instruments suffer from intrinsic background fluorescence contributed by fluorescent biological molecules such as NAD, NADH, NADP, and NADPH. In addition, current FP instruments also suffer from intrinsic AC line voltage noise. Thus, there is a need for improved fluorescence polarization instruments which are smaller, lighter, and operate using a battery pack or other low power DC power source; avoid the intrinsic background fluorescence contributed by fluorescent biological molecules such as NAD, NADH, NADP, and NADPH; and offer a simplified optics block design. In particular, with increasing prevalence of non-invasive FP tests applicable to a wide spectrum of microorganisms, to aid in diagnosis of disease, detection of exposure, or verification of vaccination, both military and civilian applications in a clinic or field setting will require portable FP instruments. The inventive apparatus satisfies this need by providing a miniaturized, portable apparatus for measuring the fluorescence polarization of a liquid sample.

SUMMARY OF THE INVENTION

The present inventive subject matter relates to a method for detecting the presence of a biological substance in a test sample, comprising the steps of:
(a) collecting a test sample selected from the group consisting of saliva, oral fluid and a bodily fluid from a subject,
(b) combining said test sample with a fluorescence-labeled ligand to said biological substance, to produce an assay solution, and
(c) measuring the change in fluorescence polarization of said assay solution.

Additionally, the inventive subject matter relates to a method for detecting the presence of an antibody in a test sample selected from the group consisting of saliva, oral fluid and a bodily fluid from a subject, comprising the steps of:
(a) combining said test sample with a fluorescence-labeled antigen to said antibody, to produce an assay solution,
(b) measuring the fluorescence polarization of a negative control solution of said fluorescence-labeled ligand, a positive control solution of said fluorescence-labeled ligand bound to a known target molecule of said ligand, or both,
(c) measuring the fluorescence polarization of said assay solution, and (d) comparing the measured fluorescence polarization of said assay solution with the measured fluorescence polarization of said negative control solution, said positive control solution, or both.

Figure 2:
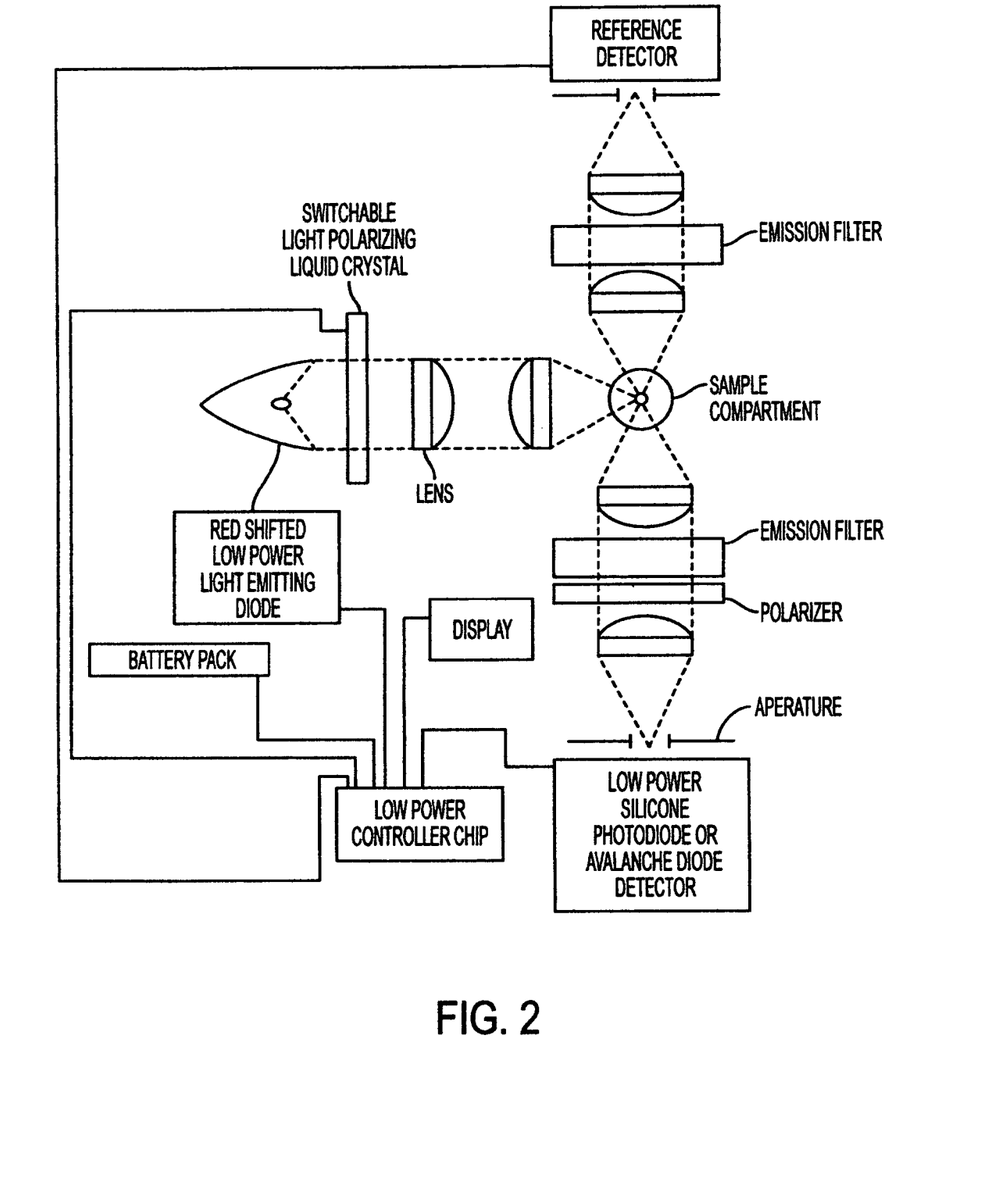
FIG. 2 is a schematic drawing which depicts a fluorescence polarization instrument according to one aspect of the inventive subject matter, with the elements labeled in text form.
Figure 3:
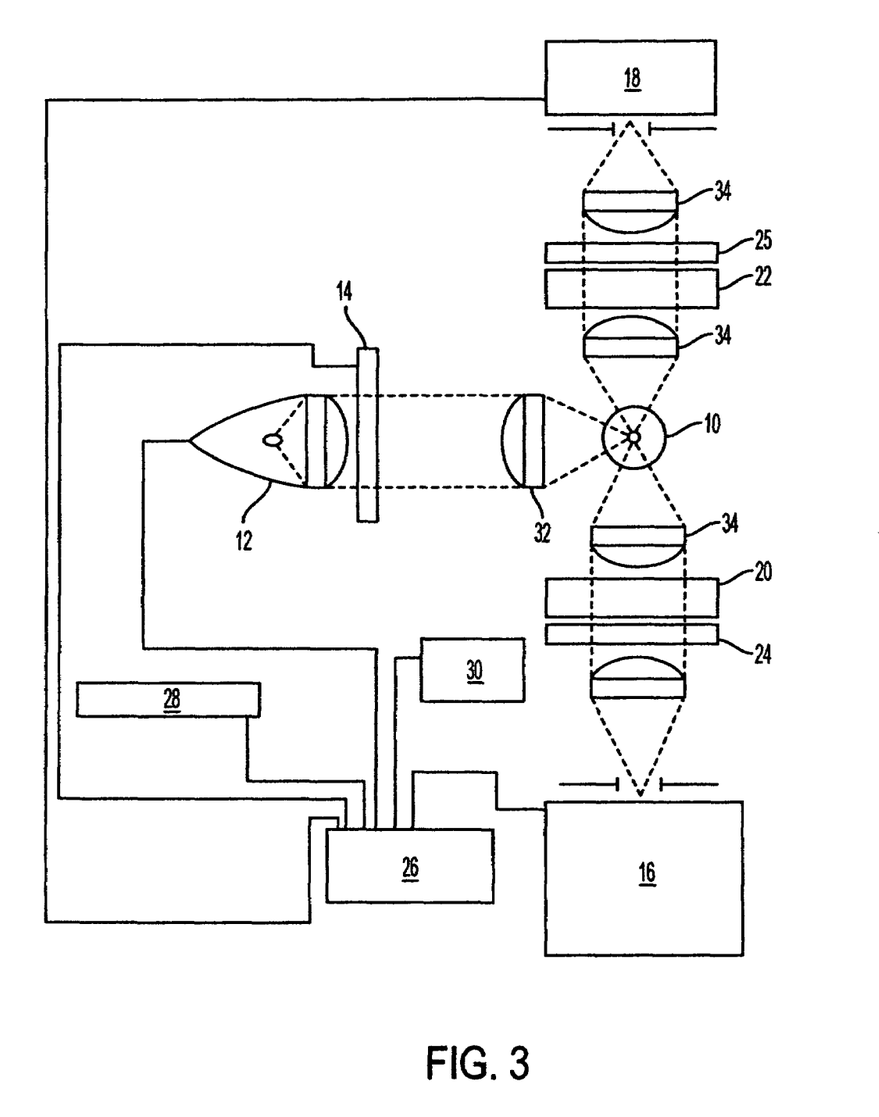
FIG. 3 is a drawing which depicts a fluorescence polarization instrument according to one aspect of the inventive subject matter, with the elements labeled with reference numbers.

The inventive subject matter further relates to an apparatus for measuring the fluorescence polarization of a liquid sample, comprising:
(A) a sample compartment (10) for containing said liquid sample;
(B) a light emitting diode light source (12) for irradiating said sample compartment (10) with excitation light;
(C) a liquid crystal (14) between said light source (12) and said sample compartment (10), wherein said liquid crystal (14) is switchable to produce different light polarization angles to said sample compartment (10);
(D) a low power primary detector (16) for detecting a polarized emission light from said sample compartment (10);
(E) a low power reference detector (18) for detecting an emission light from said sample compartment (10);
(F) a first emission filter (20), between said sample compartment (10) and said primary detector (16);
(G) a second emission filter (22), between said sample compartment (10) and said reference detector (18);
(H) a first polarizer (24) between said first emission filter (20) and said primary detector (16);
(I) a second polarizer (25) between the second emission filter (20) and the said reference detector (18);
(J) a low power controller chip (26), for processing an output from said reference detector (18) and an output from said primary detector (16), and for calculating and outputting an anisotropy value;
(K) a DC power source, comprising a battery pack (28); and
(L) a display (30) for displaying said anisotropy value, wherein said light source (12), said liquid crystal (14), said primary detector (16), said reference detector (18), said battery pack (28), and said display (30) are each operably connected to said controller chip (26).

DETAILED DESCRIPTION OF THE INVENTIVE SUBJECT MATTER

Definitions

The term "bodily fluid" as used herein refers to oral rinse expectorant, including oral mucosal transudate and gingival crevicular fluid, urine, sweat, tears, blood, serum, stool, gastric fluid, synovial fluid and phlegm.

The term "ELISA" as used herein refers to an enzyme-linked immunosorbant assay.

The term "RIA" as used herein refers to a radioimmunoassay.

The term "gingival crevicular fluid" or "GCF" as used herein refers to a transudate of blood serum found along the gingival margins of the teeth.

The term "oral mucosal transudate" or "OMT" as used herein refers to a fluid obtained from the buccal mucosal surface juxtaposed between the parotid duct and the gingival crest.

The term "oral fluid" as used herein refers to the oral fluids GCF and OMT, which arise due to hydrostatic pressure of the capillaries and venules associated with the lingual or buccal epithelium, and contain antibodies.

The term "saliva" as used herein refers to the composite of all oral fluids, and which contains a diluted mixture of antibodies from the GCF and OMT, as well as salivary gland-produced and other locally produced antibodies.

The term "fluorescence-labeled" as used herein refers to a molecule or other substance which has an associated fluorochrome, whether linked by chemical conjugation, co-produced (such as a chimeric protein translated from RNA with an integrated fluorescent protein sequence such as Green Fluorescent Protein ("GFP"), for example), or by other means known in the art. A reasonably skilled artisan will understand that there are many ways to associate a fluorochrome with a substance. Exemplary fluorochromes are discussed herein.

The term "fluorescence polarization" or "FP" as used herein refers to the effect in which visible or ultraviolet light is polarized with a filter and shines on part of a molecule, the fluorochrome, which in turn fluoresces, emitting light of a longer wavelength than the original light. FP is discussed in detail herein.

The term "anisotropy value" as used herein refers to the measured optical property of a particle, wherein its scattering behavior varies as it is rotated around its axis of symmetry.

The term "anisotropic" as used herein refers to properties which vary depending on the direction of measurement.

The term "microorganism" as used herein refers to any noncellular or unicellular organism, including colonial organisms, such as bacteria, protozoa, viruses, microfungi, rickettsia, and other similar organisms. The term "microorganism" as used herein specifically includes dormant forms of microorganisms, such as spores and other reproductive bodies and resting states.

The term "handheld" as used herein refers to an instrument which is compact enough to be used or operated while being held in the hand or hands.

The term "low power" as used herein refers to an electronic part or component which has sufficiently low power requirements to be used or operated when powered by a DC battery pack or other portable power source.

Methods of the Inventive Subject Matter

Infectious disease rates and immunization strategies continue to evolve in the United States and worldwide in response to societal needs, national defense, and evolutionary changes in the organisms producing disease. For example, anthrax has emerged as a particularly significant pathogen during the past two years.

Immunizations are performed to prevent infections. However, there are exceptions to the general strategy of routine immunization, including tuberculosis and HIV, for which population screening is most often employed. Overlapping strategies apply to some infections, such as Hepatitis B virus for example, for which both screening and vaccination are performed.

ELISA, RIA, and immunoprecipitation assays are the previously accepted methods to measure antibody levels. There is a need for rapid and accurate diagnostics, as ELISA, RIA, and immunoprecipitation are non-homogeneous assays, requiring surfaces or centrifugation steps to make the assays work.

On the other hand, FP is a homogeneous, solution-based technology that can accurately estimate concentrations of diagnostic markers, drugs and other chemicals, and infectious or biohazardous agents in body fluids or environmental samples within a few seconds to several minutes with single point standardization. FP tests currently used in clinical laboratories measure the levels of drugs, hormones, or antibiotics in blood plasma.

In addition, FP assays are used to measure different types of binding reactions, to follow proteolytic reactions with and without their inhibitors, and to measure various other enzymatic or receptor binding reactions (See, for example, Nasir M, Jolley M, *Fluorescence polarization: An analytical tool for immunoassay and drug discovery*, Comb Chem High Throughput Screen, 2:177-90 (1999)). FP is both rapid and accurate, and has no counterpart in ELISA or RIA technology.

Current tests also require blood or serum samples, which are diluted to begin serum based assays. In contrast, oral fluids do not generally require dilution.

Thus, Applicants have developed fluorescence polarization methods as diagnostic tools to assay antibodies, proteases, sugars, and nucleic acids in saliva and other oral fluids as well as bodily fluids. Fluorescence polarization provides quantitation of molecular interaction, such as antigen-antibody binding, enzymatic activity, or ribozymic activity of a single, small-volume sample, in real-time, and without prior separation or dilution of components.

Surprisingly, FP diagnostic procedures are not well known. Applicants expect the widespread use of these assays as non-invasive tests, especially as more compact, simplified fluorescence polarimeters become available. FP technology has already been miniaturized from a 27 cubic foot size, used by hospital laboratories to process nearly 1000 samples per hour, to the present 2 cubic foot commercially available portable instrument, which uses a portable single test tube, or a 96-well or 384-well benchtop instrument. FP based assays are expected to become further miniaturized in both civilian and military sectors. To our knowledge, we are the first to design FP assays for use on oral fluid samples.

Thus, the inventive subject matter relates to a method for detecting the presence of a biological substance in a test sample, comprising the steps of:

(a) collecting a test sample selected from the group consisting of saliva, oral fluid and a bodily fluid from a subject, (b) combining said test sample with a fluorescence-labeled ligand to said biological substance, to produce an assay solution, and (c) measuring the fluorescence polarization of said assay solution.

In another aspect of the inventive subject matter, said method comprises the additional steps of:

(d) measuring the fluorescence polarization of a negative control solution of said fluorescence-labeled ligand, a positive control solution of said fluorescence-labeled ligand bound to a known target molecule of said ligand, or both, and (e) comparing the measured fluorescence polarization of said assay solution with the measured fluorescence polarization of said negative control solution, said positive control solution, or both.

In yet another aspect of the inventive subject matter, said method comprises alternatively the additional steps of:

(d) measuring the background fluorescence polarization reading of said test sample; and (e) measuring the change in the fluorescence polarization of said assay solution.

In another aspect of the inventive subject matter, said biological substance is selected from the group consisting of a microorganism, a naturally-occurring or synthetic peptide, a protein, a lipid, a saccharide, a nucleic acid, an RNAase, a DNAase, a ribozyme, a prion, a pharmaceutical, an antigen, an environmental pollutant, a toxin, an abused drug, an antibody, and another catalytic entity. It is expected that methods and reagents for the preparation and/or isolation of ligand(s) to a biological substance are known to one of ordinary skill in the art. Similarly, one of ordinary skill in the art will recognize that fluorescence-labeled ligands are also prepared using standard methods and reagents.

A prion is a small proteinaceous infectious particle which resists inactivation by procedures that modify nucleic acids, and alone can transmit an infectious disease. Prion diseases are often called spongiform encephalopathies because of the post mortem appearance of the brain with large vacuoles in the cortex and cerebellum. Exemplary prion-caused or prion-associated diseases which may be detected include scrapie in sheep, transmissible mink encephalopathy in mink, chronic wasting disease in muledeer and elk, and bovine spongiform encephalopathy in cows. Humans are also believed to be susceptible to several prion diseases: Creutzfeld-Jacob Disease, Gerstmann-Straussler-Scheinker syndrome, fatal familial insomnia, Kuru, and Alpers Syndrome.

Exemplary environmental pollutants which may be detected include acetone, arsenic, asbestos, barium, benzene, cadmium, carbon monoxide, chlorinated solvents, chlorofluorocarbons, chloroform, cyanide, dichloroethylene, dioxins, endocrine disruptors, ether, ethylbenzene, furans, halons, heavy metals, hydrochlorofluorocarbons, inorganic cyanides, ketones, lead, mercury, methyl tertiary butyl ether, methyl bromide, methyl chloride, nitrogen oxides, organic cyanides, perchloroethylene, phthalates, polychlorinated biphenyls, radionuclides, radon, sulfur oxides, tetrachloroethylene, toluene, trichloroethylene, and volatile organic compounds.

Exemplary abused drugs which may be detected include marijuana, cocaine, opiates, amphetamines, phencyclidine, flunitrazepam, hallucinogenic mushrooms, gamma hydroxybutyrate, inhalants, ketamine, lysergic acid diethylamide, 3,4-methylenedioxymethamphetamine, methcathinone, methylphenidate, nicotine, caffeine, and steroids.

In a preferred embodiment, said biological substance is an antibody to a microorganism selected from the group consisting of a bacteria and a virus.

In a more preferred embodiment, said bacteria is selected from the group consisting of Bacillaceae, Mycobacteriaceae, Yersiniaceae, Rhodospirillaceae, Chromatiaceae, Chlorobiaceae, Myxococcaceae, Archangiaceae, Cystobacteraceae, Polyangiaceae, Cytophagaceae, Beggiatoaceae, Simonsiellaceae, Leucotrichaceae, Achromatiaceae, Pelonemataceae, Spirochaetaceae, Spirillaceae, Pseudomonadaceae, Azotobacteraceae, Rhizobiceae, Methylomonadaceae, Halobacteriaceae, Enterobacteriaceae, Vibrionaceae, Bacteroidaceae, Neisseriaceae, Veillonellaceae, bacterial organisms oxidizing ammonia or nitrite, bacterial organisms metabolizing sulfur and sulfur compounds, bacterial organisms depositing iron or manganese oxides, Siderocapsaceae, Methanobacteriaceae, Aerobic and facultatively anaerobic Micrococcaceae, Streptococcaceae, Anaerobic Peptococcaceae, Lactobacillaceae, Coryneform group of bacteria, Propionibacteriaceae, Actinomycetaceae, Frankiaceae, Actinoplanaceae, Dermatophilaceae, Nocardiaceae, Streptomycetaceae, Micromonosporaceae, Rickettsiaceae, Bartonellaceae, Anaplasmataceae, Chlamydiaceae, Mycoplasmataceae, and Acholeplasmataceae.

Exemplary bacteria which may be particularly relevant for public health, military, and bioterrorism testing include Bacillus anthracis, Mycobacterium tuberculosis, Yersinia pestis, Clostridium botulinum, Vibrio cholerae, Escherichia coli, Salmonella Typhi, Rancisella tularensis, and Rickettsia prowazekii.

In a most preferred embodiment, said bacteria is selected from the group consisting of Bacillus anthracis and Mycobacterium tuberculosis.

In another preferred embodiment, said virus is selected from the group consisting of Hepatitis A virus, Hepatitis B virus, Hepatitis C virus, Hepatitis D virus, Hepatitis E virus, human immunodeficiency virus, variola major, Enterovirus, Cardiovirus, Rhinovirus, Aphthovirus, Calicivirus, Orbivirus, Reovirus, Rotavirus, Abibirnavirus, Piscibirnavirus, Entomobirnavirus, Rubivirus, Pestivirus, Flavivirus, Influenzavirus, Pneumovirus, Paramyxovirus, Morbillivirus, Vesiculovirus, Lyssavirus, Coronavirus, Bunyavirus, Herpesvirus, Hantavirus, Alphavirus, Filovirus, and Arenavirus.

In another most preferred embodiment, said virus is selected from the group consisting of Hepatitis A virus, Hepatitis B virus, Hepatitis C virus, Hepatitis D virus, Hepatitis E virus, variola major, human immunodeficiency virus, Ebola virus, and Lassa virus.

In another aspect of the inventive subject matter, said fluorescence-labeled ligand is selected from the group consisting of an antigen, an antibody, a receptor, and an inhibitor, wherein said ligand is capable of specifically binding to said biological substance.

The FP Assay

ELISA, RIA, and immunoprecipitation assays are the previously accepted methods to measure antibody levels. There is a need for rapid and accurate diagnostics, as both ELISA and RIA are non-homogeneous assays, requiring surfaces or centrifugation steps to make the assays work.

Historically, radioisotope-based assays or chemiluminescence-based assays have been more sensitive, while FP has proven very useful for quantifying antigens or antibodies present in relatively large concentrations. More recently, FP sensitivity has approached that of ELISA and RIA. A comparison of some of the practical and commercial characteristics of the major types of diagnostic assays is presented in Table 1. FP is comparable to ELISA in these characteristics.

TABLE 1

Comparison of Features of Immunoassay Methods

| | Non-homogeneous | | Homogeneous | Homogeneous Fluorescence |
|---|---|---|---|---|
| Criteria | RIA | ELISA | Chemiluminescence | Polarization |
| Sensitivity | High | Moderate | High | Moderate |
| Cost | High | Low | Low | Low |
| Shelf-life | Short | Long | Long | Very long |
| Hazards | Present | Few | None | None |

In addition, FP homogeneous assay systems are robust and relatively unaffected by non-homogeneous samples like whole blood or saliva. Specificity of FP assays is generally very high, approximately 98%, compared to solid phase, non-homogeneous, formats such as ELISA, approximately 70%. In addition, non-specific binding artifacts hinder ELISA and other solid phase assays. FP has proven very useful for quantifying antigens or antibodies present in relatively large concentrations (micrograms per ml), while radioisotope-based assays or chemiluminescence-based assays have been more sensitive. However, recent advances in single-molecule fluorescence polarization will extend the range of FP assays. Therefore, its ruggedness in field settings, low cost, long reagent shelf life, few hazards, and rapidly quantitated results make FP ideal as a diagnostic tool. Applicants have developed a non-invasive oral fluid test in place of drawn blood serum.

Use of Oral Fluids

Oral fluids have been increasingly recognized as acceptable alternatives to serum for use in diagnostic tests for certain hormones, drugs, antibodies and antigens. However, diagnostic assays utilizing saliva and other oral fluids appear as entries in the National Library of Medicine MEDLARS database with a frequency of only 1 in 30 and 1 in 100, respectively, when compared to entries in which blood serum is reported. The oral cavity as an immunological entity has been reviewed with respect to oral diseases and microbiology. The use of oral fluids in diagnostic immunology includes detection of HIV; measles, mumps and rubella; hepatitis A; hepatitis B; and hepatitis C; *Helicobacter pylori*; dengue; and Chagas' disease.

Historically, the US Army Medical Research Development Command supported a contract which published one of the first reports of human salivary antibodies to indigenous bacteria. More recently, the United States Department of Agriculture has sponsored a symposium to advance non- or minimally-invasive technologies to monitor health and nutritional status in the Special Supplemental Nutrition Program for Women Infants and Children using saliva as a diagnostic tool. These considerations and continuing improvements in standardization of collection methods make saliva and oral fluids a diagnostic media of choice for the future, particularly in those instances were rapid detection in field situations is required.

Oral fluids are collected without pain, needle sticks, or religious and social prohibitions, and use of these involves minimal risk or exempt protocols for the use of human subjects. The Department of Defense has made salivary diagnostics a Future Naval Capability, and both the Office of Naval Research and the Military Infectious Disease Research Program of the US Army have funded projects to investigate the use of oral fluids or saliva to diagnose disease or monitor immunization status.

Saliva and oral fluid are distinct biochemically. They generally reflect the serum pool, but neither is a passive ultrafiltrate of serum as previously thought. The presence of mucins, the polyanionic glycoproteins that increase salivary viscosity, and oral flora have been largely responsible for the lack of popularity of oral fluids in clinical research. Recent reviews of the clinical chemistry and microbiology of saliva, the roles of saliva in health and disease, in diagnosing periodontal disease, and as a diagnostic fluid indicate the growing prominence the inventive subject matter will play in medical diagnostics.

Saliva presents several challenges for diagnostics: limited reference values have been published and the standardization of sample collection has fallen behind serum. Standardized saliva and oral fluid collection devices have only recently become available and should contribute to further investigations.

Saliva contains antibodies to various infectious agents. Some of these antibodies are derived from local production and some from the gingival crevicular fluid (hereinafter "GCF"), which is a transudate of blood serum found along the gingival margins of the teeth. Antibody containing oral fluids GCF and Oral Mucosal Transudate (OMT) arise due to hydrostatic pressure of the capillaries and venules associated with the lingual or buccal epithelium. They offer less variation than saliva and the best alternative to serum for antibody detection.

GCF is similar to serum in protein composition but is significantly lower in protein concentration, being about 3% of the protein levels in blood. GCF volume is about one percent of total saliva volume in the healthy mouth. GCF is obtained by inserting an absorbent paper into the pocket or sulcus of a tooth, between the tooth and gingiva, after clearing the supragingival plaque.

OMT is 3-4 fold higher in protein concentration than saliva based on IgG content and is collected, for example, by placing a thick pad against the buccal mucosal surface juxtaposed between the parotid duct and the gingival crest. A current OMT device design uses a salt-impregnated pad that is subsequently treated to release the antibody-containing fluid and retain the glycoproteins on the pad yielding "oral fluid". One such oral fluid collection device is commercially available and eliminates the necessity for venipuncture.

The GCF concentrations of antibodies are about one-third to one-fourth those found in blood. Oral fluid contains IgG concentrations about two-fold to four-fold that of whole saliva. Oral fluid IgG concentration varies with host factors such as HIV status, tobacco use, time after meals, and bleeding gums. Whole saliva contains a diluted mixture of these serum-derived antibodies, as well as salivary gland-produced and other locally produced antibodies. The levels of immunoglobulins in various fluid pools are shown in Table 2.

TABLE 2

Concentration of Immunoglobulins (in mg/100 ml)* in the Oral Cavity Compared to Serum

| Fluid | sIgA | IgA | IgG | IgM |
|---|---|---|---|---|
| Serum | 0.3-0.9^ | 220-230 | 1120-1250 | 80-170 |
| Gingival Fluid | 0.3-0.9^ | 80-110# | 220-1030# | 10-25# |
| Oral Mucosal Transudate | 40-410## | 8-20## | 1.5-5 | 0.8^## |
| Whole Saliva | 40-410* | 8-20* | 1.4* | 0.2* |
| Parotid Saliva | 0.2-120** | 7**-35 | 0.04-0.06** | 0.04** |

*unstimulated
**stimulated
determined in periodontitis
estimated to be equivalent to whole saliva
^##estimated from serum/saliva ratio of total saliva IgG
^estimated from serum value for secretory IgA In another aspect of the inventive subject matter, said fluorescence-labeled ligand is an antigen selected from the group consisting of a ligand to a monoclonal antibody, a ligand to a polyclonal antibody, a ligand to a chimeric antibody, a ligand to a Fab antibody fragment, and a ligand to a (Fab)2 antibody fragment.

The inventive subject matter is more specifically directed to the use of fluorescence polarization-based tests to detect antibodies to anthrax vaccine and to tuberculosis exposure, using saliva, GCF, or OMT as a test fluid. Thus, in another aspect of the inventive subject matter, said fluorescence-labeled ligand is an antigen to an antibody to *Bacillus anthracis* or *Mycobacterium tuberculosis*.

In one preferred embodiment, said antibody to *Bacillus anthracis* is a monoclonal antibody to *Bacillus anthracis* protective antigen protein.

For a rapid diagnostic for tuberculosis screening purposes, the method is analogous to that for anthrax immunization. We expect that our FP test will detect human antibodies to *m. tuberculosis* antigens such as CFP-10, ESAT-6, and MPT-63. Thus, in another preferred embodiment, said antibody to

*Mycobacterium tuberculosis* is selected from the group specific antigens consisting of CFP-10, ESAT-6, and MPT-63. However, the complete genome of *Mycobacterium tuberculosis* has been sequenced, and approximately 4000 genes have been identified in its genome (Cole, et al., Deciphering the Biology of *Mycobacterium tuberculosis* from the Complete Genome Sequence, Nature 393:537-544 (1998)). It is expected that an antibody to any one of the gene products of the genes of *Mycobacterium tuberculosis* may be utilized to produce an antibody within the scope of the inventive subject matter. The methods for isolating such gene products and for producing antibodies to such gene products, whether monoclonal antibodies or polyclonal antibodies, are known to those of ordinary skill in the art, requiring no more than routine experimentation to produce.

Applicants have developed FP assays to make rapid routine testing possible. Because of homogeneous molecule-molecule interactions, FP assays offer rational approaches for the detection of antibodies, for example for assays for tuberculosis exposure or infection, or anthrax vaccination status, using saliva, gingival crevicular fluid, or oral fluid. Thus, a rapid FP assay on oral fluid to detect tuberculosis antibodies replaces the invasive Tuberculosis Skin Test (TST) injection and precludes the need to return after 2-3 days for the TST reading. We expect that FP results will also provide scientific justification for changing the schedule or route of administration of the existing anthrax vaccine or help in establishing guidelines for future recombinant anthrax vaccines. Our expectation is based on the observation that antibodies similar to those in serum can be detected in oral fluids such as saliva, gingival crevicular fluid, or oral mucosal transudate, depending upon the fluid and type of immunoglobulin measured.

Anthrax. In an anthrax infection, protective antigen protein, along with two other proteins, lethal factor and edema factor, are released by the bacterium *Bacillus anthracis*. Protective antigen protein interacts with these other two components to produce the active anthrax toxin. A concise summary of the details of this toxin formation and action is given in a recent paper, Sellman B, Mourez M, Collier R, Dominant-negative mutants of a toxin subunit: An approach to therapy of anthrax, Science 292:695-7 (2001).

The complete DNA and protein sequence of protective antigen protein and its three-dimensional structure from x-ray crystallography are available. Information on the biological functions of the four domains of protective antigen protein is also available, and epitopes within the domains can be selected for antigenic properties. In earlier animal studies and in natural human infections, it was shown that individuals who survived an infection produced antibodies against protective antigen protein. The current human vaccine licensed in the United States for anthrax, Anthrax Vaccine Adsorbed (hereinafter "AVA"), contains aluminum hydroxide adjuvant and consists mostly of protective antigen protein from an attenuated, non-encapsulated strain of the bacterium. Several recombinant protective antigen protein experimental plasmids have been produced throughout the world. In the future, if recombinant protective antigen protein alone is shown to afford protection in appropriate animal models, it is expected to become the next-generation vaccine.

Military personnel are immunized to varying degrees with AVA, and serve as our source of oral fluids and serum. Verification of vaccine response will focus on detection of antibodies in humans to the protective antigen protein, which is contained in the current vaccine.

Since one expects immunization to develop high titer antibody against an injected antigen in most immunized individuals, anthrax immunization status is a first model for a non-invasive FP test to use with saliva, other oral and bodily fluids. We expect that there is ample antibody titer in all oral fluids to give us the relative values for each, and we expect that routine testing will provide information to form the basis for selection of the most appropriate fluid to use for FP assays for detection of antibodies.

Tuberculosis

Applicants have developed a rapid, 1-2 minute, non-invasive diagnostic tool for tuberculosis screening. FP tests are designed to detect tuberculosis-specific antibodies in saliva, oral or bodily fluids, which serve as an indicator of infection with *M. tuberculosis*. Specific epitopes are known to exist for several immunodominant antigens, defined by monoclonal antibodies used in human serological studies. Small recombinant proteins or peptides containing specific epitopes of early infection stage antigenic tuberculosis proteins form the basis for rapid FP assays to capture patient antibodies.

Numerous tuberculosis antigens have been purified from cultures of virulent and non-virulent strains of both *Mycobacterium tuberculosis* and *M. bovis*. Useful recombinant proteins have been produced for ELISA tests. Affinity labeled *M. tuberculosis* proteins suitable for FP, and that react with specific monoclonal antibodies used to titer sera from human tuberculosis patients, have been developed. In addition, the total DNA sequence of *M. tuberculosis* is published, for which an index and references are available. Peptides of clinical significance are labeled with a fluorescent dye and tested with saliva and sera from negative controls and patients with confirmed tuberculosis. We expect that FP tests will be used to measure antibodies in oral fluids in any clinical setting, and results made available to the doctor and patient during that same visit.

In a preferred embodiment, said fluorescence-labeled ligand has a molecular weight less than about 30,000 Daltons.

In a more preferred embodiment, said fluorescence-labeled ligand has a molecular weight less than about 20,000 Daltons.

In a most preferred embodiment, said fluorescence-labeled ligand has a molecular weight less than about 10,000 Daltons.

In another aspect of the inventive subject matter, said fluorescence-labeled ligand comprises a fluorochrome selected from the non-limiting group consisting of 7-AAD, Acridine Orange, Alexa 488, Alexa 532, Alexa 546, Alexa 568, Alexa 594, Aminonapthalene, Benzoxadiazole, BODIPY 493/504, BODIPY 505/515, BODIPY 576/589, BODIPY FL, BODIPY TMR, BODIPY TR, Carboxytetramethylrhodamine, Cascade Blue, a Coumarin, $Cy^2$, $CY^3$, $CY^5$, $CY^9$, Dansyl Chloride, DAPI, Eosin, Erythrosin, Ethidium Homodimer II, Ethidium Bromide, Fluorescamine, Fluorescein, FTC, GFP (yellow shifted mutants T203Y, T203F, S65G/S72A), Hoechst 33242, Hoechst 33258, IAEDANS, an Indopyras Dye, a Lanthanide Chelate, a Lanthanide Cryptate, Lissamine Rhodamine, Lucifer Yellow, Maleimide, MANT, MQAE, NBD, Oregon Green 488, Oregon Green 514, Oregon Green 500, Phycoerythrin, a Porphyrin, Propidium Iodide, Pyrene, Pyrene Butyrate, Pyrene Maleimide, Pyridyloxazole, Rhodamine 123, Rhodamine 6G, Rhodamine Green, SPQ, Texas Red, TMRM, TOTO-1, TRITC, and YOYO-1. Other non-limiting examples of fluorochromes contemplated within the scope of the inventive subject matter include vitamin $B_{12}$, flavin-adenine dinucleotide, and nicotinamide-adenine dinucleotide.

In a preferred embodiment, said fluorescence-labeled ligand comprises a fluorochrome having a fluorescence emission spectra lifetime greater than about 3 nanoseconds.

In a more preferred embodiment, said fluorescence-labeled ligand comprises a fluorochrome having a fluorescence emission spectra lifetime greater than about 4 nanoseconds.

In a most preferred embodiment, said fluorescence-labeled ligand comprises a fluorochrome having a fluorescence emission spectra lifetime greater than about 5 nanoseconds.

Selection of the appropriate fluorochrome, whether from this exemplary list or from other fluorochromes known in the art or yet to discovered, is within the knowledge of the ordinarily-skilled artisan, using no more than routine experimentation.

In a particular aspect, the inventive subject matter relates to a method for detecting the presence of an antibody in a test sample selected from the group consisting of saliva, oral fluid and a bodily fluid from a subject, comprising the steps of:
 (a) combining said test sample with a fluorescence-labeled antigen to said antibody, to produce an assay solution,
 (b) measuring the fluorescence polarization of a negative control solution of said fluorescence-labeled ligand, a positive control solution of said fluorescence-labeled ligand bound to a known target molecule of said ligand, or both,
 (c) measuring the fluorescence polarization of said assay solution, and
 (d) comparing the measured fluorescence polarization of said assay solution with the measured fluorescence polarization of said negative control solution, said positive control solution, or both.

Inventive Apparatus

When a fluorescent liquid sample is irradiated with excitation light, the sample radiates an emission light from which the polarization, P, is determined in accordance with the expression: $I(Z)-I(Y)/I(Z)+I(Y)$, where $I(Z)$ is the measured intensity of one polarization component of the emitted light at a first polarization angle when the liquid sample is irradiated with polarized excitation light at the first polarization angle, and where $I(Y)$ is the measured intensity of the polarization component of emitted light at the first polarization angle when the liquid sample is irradiated with polarized excitation light at a second polarization angle perpendicular with respect to said first polarization angle. Using a common fluorochrome, the difference between the polarization of a reference or control sample and the polarization of a sample of interest is determined by differences in the mass of a molecule attached to the fluorochrome, as discussed in detail above. Thus, the inventive subject matter further relates to an apparatus for measuring the fluorescence polarization of a liquid sample, comprising:
 (A) a sample compartment (10) for containing said liquid sample;
 (B) a light emitting diode light source (12) for irradiating said sample compartment (10) with excitation light;
 (C) a liquid crystal (14) between said light source (12) and said sample compartment (10), wherein said liquid crystal (14) is switchable to produce different light polarization angles to said sample compartment (10);
 (D) a low power primary detector (16) for detecting a polarized emission light from said sample compartment (10);
 (E) a low power reference detector (18) for detecting an emission light from said sample compartment (10);
 (F) a first emission filter (20), between said sample compartment (10) and said primary detector (16);
 (G) a second emission filter (22), between said sample compartment (10) and said reference detector (18);
 (H) a first polarizer (24) between said first emission filter (20) and said primary detector (16);
 (I) a second polarizer (25) between the second emission filter (20) and the said reference detector (18);
 (J) a low power controller chip (26), for processing an output from said reference detector (18) and an output from said primary detector (16), and for calculating and outputting an anisotropy value;
 (K) a DC power source, comprising a battery pack (28); and
 (L) a display (30) for displaying said anisotropy value,
  wherein said light source (12), said liquid crystal (14), said primary detector (16), said reference detector (18), said battery pack (28), and said display (30) are each operably connected to said controller chip (26).

In an aspect of the inventive subject matter, said polarizer (24) is a vertical polarizer.

In another aspect of the inventive subject matter, said apparatus further comprises:
 (i) one or more excitation light focusing lense(s) (32) between said light source (12) and said sample compartment (10), for focusing excitation light to said sample compartment (10);
 (ii) one or more emission light focusing lense(s) (34) between said sample compartment (10) and said reference detector (18), for focusing emitted light to said reference detector (18); and
 (iii) one or more emission light focusing lense(s) (34) between said sample compartment (10) and said primary detector (16), for focusing emitted light to said primary detector (16).

In another aspect of the inventive subject matter, said light emitting diode emits red-shifted excitation light.

The inventive apparatus represents several improvements over the prior art exemplified by U.S. Pat. No. 4,516,856 to Popelka, et al.:

1) in a preferred embodiment, it is miniaturized so that its preferred overall dimensions are not larger that about 7 inches long, about 4 inches wide, and about 2 inches thick. Thus, the inventive subject matter is optionally roughly 50 times smaller than the prior art instruments, is easily portable for field use, and is considered to be a handheld instrument. Thus, in another aspect of the inventive subject matter, said apparatus is handheld.

2) its light source is a light emitting diode that uses very little power compared to the prior art tungsten halogen lamp, and the light source is red-shifted to avoid the intrinsic background fluorescence contributed by fluorescent biological molecules such as NAD, NADH, NADP and NADPH.

3) it uses a low power consumption silicone photodiode or avalanche diode detector that avoids the high voltage and high power usage of the prior art photomultiplier type detector.

4) it uses a low power consumption controller chip that avoids the high power consumption of the prior art CPU.

5) it uses a battery pack to isolate it from line voltage noise and its design is intrinsically "quiet" compared to the prior art AC line attached machines.

6) the optics block design is simplified by use of a single light polarizing liquid crystal that operates on the off/on mode to give either vertical polarization or no light to the sample excitation light, and which in a preferred embodiment is vertical polarization.

In an aspect of the inventive apparatus, the prior art excitation filter is omitted for maximum light throughput. A single horizontal polarizer reading at 90 degrees to the excitation path allows reading of horizontal polarization by the primary detector when the excitation liquid crystal polarizer is off, i.e. the LCD is passing vertically polarized light. A single vertical polarizer is placed ahead of the reference detector at 90 degrees to the excitation path directly across from the primary detector, which collects horizontal fluorescence intensity when the LCD is off, i.e. is passing vertically polarized light. The output from reference and primary detectors allows for calculation of anisotropy values of the sample. Emission filters in the detector paths shield the detectors from scattered excitation wavelengths. This symmetrical arrangement allows for bias correction in the detector arm due to detector response when LED is off, i.e. passing only vertically polarized light, and allows for balancing the electronics when the LED is on, i.e. no light passing through the LED.

As will be understood by one of ordinary skill in the art, the sample tube used with said apparatus optionally has a rectangular or substantially circular peripheral cross-sectional configuration, as may be convenient when optimizing the design of the instrument. Further, it is preferred, but not required, that the excitation light be focused substantially at the center of the sample. In addition, it is preferred, but not required, that the emission filter pass emitted light corresponding substantially to the emission band of the fluorescent sample. Optimization of these and other parameters of the inventive apparatus are known to one of ordinary skill in the art.

EXAMPLES

The following examples are illustrative of the present inventive subject matter and are not intended to be limitations thereon. Unless otherwise indicated, all percentages are based upon 100% by weight of the final composition.

Example 1

Fluorescence Polarization Assays in Saliva and Oral Fluids

The following example illustrates an exemplary fluorescence polarization assay in saliva or oral fluid, provided according to the present inventive subject matter.

In FP based assays, visible or ultraviolet light is polarized with a filter and shines on part of a molecule, the fluorochrome, that in turn fluoresces, emitting light of longer wavelength whose signal is captured and recorded. The emitted light recorded stays more polarized in solutions when there are slower turning, large molecule-fluorochrome complexes than when there are smaller labeled molecules. Different fluorochromes can be chosen to accommodate molecules of different sizes up to $10^7$ kDa molecular weight.

In a direct binding assay, combining fluorescently labeled antigen or peptide with antibody results in an increase in FP, as measured in arbitrary millipolarization (hereinafter "mP") units. This is illustrated in Table 3.

TABLE 3

Millipolarization Values for Fluorescence Polarization Assay

| Antigen* + Antibody (low mP value) | => | Antigen* – Antibody Complex (high mP value) |
|---|---|---|

*tagged with fluorescent label

The smaller the fluorescent antigen, the greater the increase in mP units that is measured upon binding to its corresponding antibody, since mP depends upon the partial specific volume, which is related to approximate molecular weight in solution of the labeled substance. The dependence is not linear, but varies according to the Perrin equation.

Thus, for example, the difference in FP between a fluorescent antigen of 10 kDa initially and the fluorescent complex consisting of antigen and immunoglobulin G, 10 kDa+150 kDa=160 kDa, allows for measurement of a change using less than saturating antibody concentration.

FP antigen-antibody binding assays require only the mixing of fluorescent reagent, containing antigen, with a sample containing antibody, in a liquid buffer. In a rapid diagnostic format, essentially two FP readings are necessary: a baseline, negative control reading and a reading after a specified time. The FP value increases over time as binding of antigen and antibody occurs, until limited by the exhaustion of free antibody or antigen in a test sample. A distinct advantage to FP assays is that they can accommodate somewhat cloudy solutions, such as bacterial suspensions, and tolerate a variation in total fluorescence that may be found in oral fluids.

Unlike serum, the pH of saliva often drops to pH 4. As the pH decreases below pH 8, fluorescein intensity drops dramatically to an extent that would affect FP measurements. To avoid this effect, other fluorescent dyes that are considerably brighter, more photo-stable, and largely independent of pH can be substituted. Such fluorescent dyes have relaxation times and absorption and emission spectral characteristics similar to fluorescein, and are available in various chemical forms for labeling.

As contemplated by the inventive subject matter, a preferred fluorescent dye has a fluorescence emission spectra lifetime greater than about 3 nanoseconds. In a more preferred embodiment, said fluorescent dye has a fluorescence emission spectra lifetime greater than about 4 nanoseconds. In a most preferred embodiment, said fluorescent dye has a fluorescence emission spectra lifetime greater than about 5 nanoseconds.

A fluorescent label used in the inventive subject matter is any environment-sensitive probe whose fluorescence lifetime changes upon binding to another molecule. Exemplary fluorescent labels include 7-AAD, Acridine Orange, Alexa 488, Alexa 532, Alexa 546, Alexa 568, Alexa 594, Aminonapthalene, Benzoxadiazole, BODIPY 493/504, BODIPY 505/515, BODIPY 576/589, BODIPY FL, BODIPY TMR, BODIPY TR, Carboxytetramethylrhodamine, Cascade Blue, a Coumarin, $Cy^2$, $Cy^3$, $Cy^5$, $Cy^9$, Dansyl Chloride, DAPI, Eosin, Erythrosin, Ethidium Homodimer II, Ethidium Bromide, Fluorescamine, Fluorescein, FTC, GFP (yellow shifted mutants T203Y, T203F, S65G/S72A), Hoechst 33242, Hoechst 33258, IAEDANS, an Indopyras Dye, a Lanthanide Chelate, a Lanthanide Cryptate, Lissamine Rhodamine, Lucifer Yellow, Maleimide, MANT, MQAE, NBD, Oregon Green 488, Oregon Green 514, Oregon Green 500, Phycoerythrin, a Porphyrin, Propidium Iodide, Pyrene, Pyrene Butyrate, Pyrene Maleimide, Pyridyloxazole, Rhodamine 123, Rhodamine 6G, Rhodamine Green, SPQ, Texas Red, TMRM, TOTO-1, TRITC, and YOYO-1. Other non-limiting examples of fluorochromes contemplated within the scope of the inventive subject matter include vitamin $B_{12}$, flavin-adenine dinucleotide, and nicotinamide-adenine dinucleotide.

The characteristics of fluorochromes are known to persons of ordinary skill in the art. See, for example, Brismar, et al., *Spectra and Fluorescence Lifetimes of Lissamine Rhodamine, Tetramethylrhodamine Isothiocyanate, Texas Red, and Cyanine 3.18 Fluorophores*, J. Histochem. Cytochem. 43:699 (1995); Darzynkiewicz, et al., *Flow Cytometery*, Methods in Cell Biology, Second Edition, Part B, pg. 628 (1994); B. L. Sailer, et al., *Differential Effects of Deuterium oxide on the Fluorescence Lifetimes and Intensities of Dyes with Different Modes of Binding to DNA*, J. Histochem. Cytochem. 45:165 (1997); A. S. Verkman, et al., *Synthesis and Characterization of Improved Chloride-Sensitive Fluorescent Indicators for Biological Applications*, Anal. Biochem. 178:355 (1989); R. F. Chen, et al., *Atlas of Fluo-* rescence Spectra and Lifetimes of Dyes Attached to Protein, Anal. Lett. 18:393 (1985); B. K. Nunnally, et al., *Characterization of Visible Dyes for Four-Decay Fluorescence Detection in DNA Sequencing*, Anal. Chem. 69:2392 (1997); Kirschstein, et al., *Detection of the Delta F508 Mutation in the Cftr Gene by Means of Time-resolved Fluorescence Methods*, Bioelectrochem. Bioenerg. 48:415-421 (1999); Jameson, et al., *Fluorescent Nucleotide Analogs: Synthesis and Applications*, Methods Enzymol. 278:363-390 (1997); Chen R F, *Fluorescence lifetime reference standards for the range 0.189 to 115 nanoseconds*, Anal. Biochem. 57:593-604 (1974); Weltman, et al., *N-(3-pyrene)maleimide: a long lifetime fluorescent sulfhydryl reagent*, J. Biol. Chem. 248:3173-3177 (1973); and Schwille, P., et. al., *Fluorescence correlation spectroscopy reveals fast optical excitation-driven intramolecular dynamics of yellow fluorescent proteins*, Proc. Natl. Acad. Sci. USA 97:151-156 (2000).

Fluorescence emission spectra lifetimes for representative fluorochromes are provided in Table 4.

TABLE 4

| Fluorochrome Name | Fluorescence emission spectra lifetime |
|---|---|
| Acridine Orange (DNA) | 3.00 nsec |
| Acridine Orange (RNA) | 13.00 nsec |
| Alexa 488 | 4.13 nsec |
| Alexa 568 | 3.61 nsec |
| Alexa 594 | 3.90 nsec |
| Alexa 546 | 4.00 nsec |
| Alexa 532 | 4.00 nsec |
| BODIPY FL | 5.70 nsec |
| BODIPY TR | 5.40 nsec |
| BODIPY TMR | 5.55 nsec |
| BODIPY 505/515 | 5.90 nsec |
| BODIPY 493/504 | 5.90 nsec |
| BODIPY 576/589 (EtOH) | 5.00 nsec |
| BODIPY 576/589 ($H_2O$) | 1.00 nsec |
| coumarin | 3.03 nsec |
| $Cy^2$ | 0.60 nsec |
| $CY^3$ | 1.36 nsec |
| Dansyl Chloride | 13.80 nsec |
| DAPI | 4.00 nsec |
| Ethidium Bromide (DNA) | 19.00 nsec |
| Ethidium Homodimer II (DNA) | 10.00 nsec |
| Fluorescein | 4.10 nsec |
| Fluorescamine | 6.91 nsec |
| GFP (yellow shifted mutants T203Y, T203F, S65G/S72A) | 3.80 nsec |
| Hoechst 33258 | 3.50 nsec |
| Hoechst 33242 | 2.30 nsec |
| IAEDANS | 21.19 nsec |
| Lissamine Rhodamine | 2.94 nsec |
| MANT | 9.0 nsec |
| MQAE | 21.60 nsec |
| Oregon Green 488 | 4.20 nsec |
| Oregon Green 500 | 4.10 nsec |
| Oregon Green 514 | 4.20 nsec |
| Propidium Iodide (DNA) | 13.20 nsec |
| pyrene butyrate | 115.00 nsec |
| pyrene maleimide | 100.00 nsec |
| Rhodamine Green | 4.30 nsec |
| Rhodamine 123 | 4.20 nsec |
| Rhodamine 6G | 4.09 nsec |
| SPQ | 25.30 nsec |
| Texas Red | 4.50 nsec |
| TOTO-1 (DNA) | 2.20 nsec |
| TRITC | 3.32 nsec |
| TMRM | 2.20 nsec |
| YOYO-1 (DNA) | 2.10 nsec |
| 7-AAD (DNA) | 0.80 nsec |

In a preferred embodiment, said fluorescence-labeled ligand comprises a fluorochrome having a fluorescence emission spectra lifetime greater than about 3 nanoseconds.

In a more preferred embodiment, said fluorescence-labeled ligand comprises a fluorochrome having a fluorescence emission spectra lifetime greater than about 4 nanoseconds.

In a most preferred embodiment, said fluorescence-labeled ligand comprises a fluorochrome having a fluorescence emission spectra lifetime greater than about 5 nanoseconds.

Selection of a fluorescent label for use in particular circumstances is known to the ordinarily skilled artisan, using no more than routine experimentation for the purposes of optimization.

Example 2

Fluorescent Polarization Assay for Tuberculosis Exposure

The following example illustrates an exemplary fluorescent polarization assay for tuberculosis exposure, provided according to the present inventive subject matter.

Vaccination for tuberculosis occurs in most of the world using Bacille Calmette-Guerin (hereinafter "BCG") vaccine, with the exception of the United States. The TST used for tuberculosis screening requires two visits to the clinic 48-72 hours apart, the first for administration of the test material, and a second visit where the TST is read and recorded by a trained technician or medical professional.

For an exemplary rapid diagnostic screening for anthrax immunization status, an immune system stimulating part of the vaccine will be used to screen immunized individuals. In a preferred embodiment of this method, a small antigen, preferably less than 10,000 Da molecular weight, is labeled with a fluorescent dye while retaining its antigenic determinant. Such a small antigen is also the target epitope of immunodominant antibody(s) in the host. We expect that in an anthrax immunization status test, an exemplary target epitope is the highly antigenic region in the protective antigen protein molecule identified in the mouse model.

Research on tuberculosis antigens has also progressed to the point that suitable protein or peptide antigens of less than about 10 kDa are chosen for use in FP assays. The heterogeneity of the human response to different *M. tuberculosis* proteins requires the use of immunodominant epitopes from several antigens, for example CFP-10, ESAT-6, MPT-63 and others known to those of ordinary skill in the art.

Thus, a patient is suspected to have been exposed to tuberculosis. A saliva, oral or a bodily fluid test sample is collected, the test sample is combined with a fluorescence-labeled ligand to tuberculosis bacteria antibodies, the fluorescence polarization of a negative control solution of said fluorescence-labeled ligand and the test sample are measured, and the presence or absence of tuberculosis antibodies is determined.

Example 3

Fluorescence Polarization Assay for Anthrax Vaccination

The following example illustrates an exemplary fluorescence polarization assay for anthrax vaccination, provided according to the present inventive subject matter.

Vaccination for anthrax occurs for all Department of Defense personnel deploying to at-risk areas of operation. The United States Armed Forces anthrax vaccination program currently uses the AVA vaccine. As a result, some subjects have greater than 750 micrograms/ml anti-AVA IgG per ml of serum after five or six subcutaneous doses of vaccine and a titer up to 1:4000 after three doses. Titers of this magnitude mean anti-AVA antibody can be detected in saliva. The serum anthrax enzyme-linked immunosorbant assay is the current gold standard diagnostic test, but requires a laboratory setting, trained personnel, specialized equipment, and up to 8 hours to quantitate the results.

Applicants have developed an FP assay for anthrax immunization which is straightforward and based on the fact that individuals are immunized with a prescribed quantity of antigen, at defined intervals, and in the same manner, by injection with the same antigen. The sequence, x-ray structure, and biological functions of protective antigen protein have been published, which provides relevant peptides to label for FP assays.

Thus, it is necessary to determine the immunization status of patient in need of immunity. A saliva, oral or bodily fluid test sample is collected, the test sample is combined with a fluorescence-labeled ligand to anthrax bacteria antibodies, the fluorescence polarization of a negative control solution of said fluorescence-labeled ligand and the test sample are measured, and the presence or absence of anthrax antibodies is determined.

Example 4

Fluorescence Polarization Assay for Homocysteine Metabolites

The following example illustrates an exemplary fluorescence polarization assay for homocysteine metabolites, provided according to the present inventive subject matter. Homocysteine metabolites are involved in the transsulfuration and transmethylation pathways, and are believed to serve as markers for cardiovascular diseases, vascular stroke, tissue damage resulting from cell damage or cell death due to necrosis or apoptosis, neuronal mediated tissue damage or diseases, neural tissue damage resulting from ischemia and reperfusion injury, neurological disorders and neurodegenerative diseases, age-related macular degeneration, AIDS and other immune diseases, arthritis, atherosclerosis, cachexia, cancer, degenerative diseases of skeletal muscle involving replicative senescence, diabetes, head trauma, immune senescence, inflammatory bowel disorders, muscular dystrophy, osteoarthritis, osteoporosis, chronic pain, acute pain, neuropathic pain, nervous insult, peripheral nerve injury, renal failure, retinal ischemia, septic shock, skin aging, altered circadian rhythmicicty, obesity, sickle cell anemia, cystic fibrosis, diseases or disorders relating to lifespan or proliferative capacity of cells, and diseases or disease conditions induced or exacerbated by cellular senescence.

Thus, a patient is suspected to suffer from a disorder marked by the presence or absence of a homocysteine metabolite. A saliva, oral or bodily fluid sample is collected, the test sample is combined with a fluorescence-labeled homocysteine metabolite and a high affinity antibody to the homocysteine metabolite, the fluorescence polarization of a negative control solution of said fluorescence-labeled ligand and the test sample are measured, and the presence or absence of the homocysteine metabolite is determined in a competition assay.

Prophetic Example 5

Miniaturized Handheld Fluorescence Polarimeter a. Test Time: An instrumental assay that will give a quantitative measurement, and simple yes/no indication, of a specific marker antibody in saliva or oral fluids for detection of Mtb and for evaluation of immune response to the anthrax vaccine. Results will develop under 5 minutes compared to the 1-2 days for Enzyme-Linked Immunosorbent Assay (ELISA) testing or the 3-day turnaround time for the current tuberculin skin test (TST).

b. Power Source: Hand-held instrument may be operated with batteries or with portable electrical sources if available.

c. Unique Test Features: FP is independent of sample condition; i.e. requires no sample clean-up, purification or concentration steps in process, and is unaffected by sample contamination or background interferences. This feature sets FP apart from real-time PCR or other fluorescence-based micro-array systems.

d. Required Training: Test may be administered by minimally trained personnel.

e. Scope of use: May be used in far-forward field settings to monitor exposure to infectious diseases or biological warfare agents, and also in general clinical settings to screen for disease exposure. Anthrax antibody test can be used to monitor vaccine efficacy in immunized DOD personnel and emergency first responders in this and other countries. A tuberculosis (TB) assay will be used to screen all DOD personnel, civilian medical and laboratory workers, others at risk and major immigration points of entry. Third-world countries are sorely in need of a rapid, inexpensive TB screening field test. Further development could lead to a rapid, hand-held detection device for biological warfare agents and other militarily relevant diseases.

| Final Specifications for FP Hand-Held Instrument | NIDBR-Argonne National Laboratory Miniaturized Fluorescence Polarimeter<br>TBD = to be determined |
|---|---|
| Versatility: | Air, water, soil, food, biological fluid samples minimum sample ~0.5 ml |
| Data Display: | Green (deploy; no active respirator) green word deploy<br>Red (deploy; active respirator) red word respirator<br>Yellow (error) yellow word redo<br>Keyboard and LED display<br>Internal quantitation table with RS232 out for computer |
| Data Communication: | Uplink to comsat with data quantitation |
| Dynamic Range: | 5 orders of magnitude linear between 10 pM and 100 nM |
| Detector: | Silicaone photodiode or avalanche diode |
| Polarization type: | LCD and polarizing film |
| Calibration Type: | Auto calibrate with auto on during sample insertion. Single-point and Blank (multiple blanks possible if necessary). |
| Warm-up Time: | 5 seconds. Auto on with sample insertion. Sleep after 1 min. Auto-off after 5 min. |
| Power: | Battery operated. Adapter to external power supply. |
| Measurements per TBA Battery Set: | >1,000 |
| Alarms: | Low battery |
| Auto Shutoff: | Device powers down after 90 seconds of inactive use |
| Cuvette: | Current glass cuvette used in TDx Flx instrument |
| Size: | 7.25" L × 3.5" W × 1.75" H (18.4 cm × 8.9 cm × 4.45 cm) (Maximum) |
| Weight: | 14 oz. (0.4 kg) (Maximum) |
| Temperature Range: | 41-104° F.; 5-40° C. |
| Case: | Meets IP 67 Standard, dustproof and waterproof |

| | |
|---|---|
| Maintenance: | Replace batteries and keep sample well clean |
| Discrete Sample Readings: | Averaged over 5 seconds |
| Regulatory: | CE |
| Ruggedness: | No moving parts |
| Model Specifications | |
| Channels: | Channel Fluorescein<br>Excitation: 485 nm with a bandwidth (half height) of 10 nm<br>Emission: 532 nm with a bandwidth (half height) of 10 nm |
| Stability: | Less than 1 mP Standard Deviation at 1 nM Fluorescein |
| User Interface: | Keyboard and LED display in addition to red, green, yellow lights |
| Selection of Common Pathogens: | Standard curves built-in for measurement of top 20 bio-threats<br>Color code + lettering + smart chip to set instrument to correct test parameters for detection of each agent |

Prototype II is to be designed and built to perform at least as well as existing-FP instruments. Final specifications are to be achieved in later versions of the hand-held instrument, and under separate contract.

The inventive subject matter being thus described, it will be obvious that the same may be modified or varied in many ways. Such modifications and variations are not to be regarded as a departure from the spirit and scope of the inventive subject matter and all such modifications and variations are intended to be included within the scope of the following claims.

We claim:

1. An apparatus for measuring the fluorescence polarization of a liquid sample, comprising:
   (A) a sample compartment for containing said liquid sample;
   (B) a light emitting diode light source for irradiating said sample compartment with excitation light;
   (C) a liquid crystal between said light source and said sample compartment, wherein said liquid crystal is switchable to produce different light polarization angles to said sample compartment;
   (D) a low power primary detector for detecting a polarized emission light from said sample compartment;
   (E) a low power reference detector for detecting an emission light from said sample compartment;
   (F) a first emission filter, between said sample compartment and said primary detector;
   (G) a second emission filter, between said sample compartment and said reference detector;
   (H) a first polarizer between said first emission filter and said primary detector;
   (I) a second polarizer between the second emission filter and the said reference detector;
   (J) a low sower controller chip, for processing an output from said reference detector and an output from said primary detector, and for calculating and outputting an anisotropy value;
   (K) a DC power source, comprising a battery pack; and
   (L) a display for displaying said anisotropy value, wherein said light source, said liquid crystal, said primary detector, said reference detector, said battery pack, and said display are each operably connected to said controller chip.

* * * * *